United States Patent [19]

Koch et al.

[11] Patent Number: 5,197,987
[45] Date of Patent: Mar. 30, 1993

[54] KNEE JOINT PROSTHESIS

[75] Inventors: Rudolf Koch, Frauenfeld; Robert M. Streicher, Winterthur, both of Switzerland

[73] Assignee: Sulzer Brothers Limited, Winterthur, Switzerland

[21] Appl. No.: 820,357

[22] Filed: Jan. 14, 1992

[30] Foreign Application Priority Data

Jan. 18, 1991 [CH] Switzerland .................. 00144/91

[51] Int. Cl.⁵ .............................................. A61F 2/38
[52] U.S. Cl. .................................. 623/20; 623/18
[58] Field of Search .................. 623/18, 20, 22, 23

[56] References Cited

U.S. PATENT DOCUMENTS

| | | | |
|---|---|---|---|
| 4,085,466 | 4/1978 | Goodfellow et al. | 623/20 |
| 4,224,697 | 9/1980 | Murray et al. | 623/20 |
| 4,340,978 | 7/1982 | Buechel | 623/20 |

FOREIGN PATENT DOCUMENTS 1527498 10/1978 United Kingdom .

*Primary Examiner*—Randy C. Shay
*Attorney, Agent, or Firm*—Kenyon & Kenyon

[57] ABSTRACT

The knee joint prosthesis is formed of a tibia metal plate which can be attached to a tibia and a femur part which can be secured in a femur. An intermediate plastic part is provided on the tibia metal plate to receive the femur part in bearing relation. In order to reduce abrasion of the intermediate plastic part, support members of hard material are distributed in the bearing surface of the intermediate plastic part to receive the femur part thereon. The bearing surfaces of the support members are integrated in the bearing surface of the intermediate part and are provided with dual surfaces to receive different bearing surfaces of the femur part, each of which has a different radius of curvature.

10 Claims, 3 Drawing Sheets

KNEE JOINT PROSTHESIS

This invention relates to a knee joint prosthesis. More particularly, this invention relates to a tibia part of a knee joint prosthesis.

Heretofore, various types of knee joint prostheses have been proposed. For example, European Patent Application 0 346 183 describes a knee joint prosthesis composed of multiple parts including a femur part having condyle surfaces, a tibia part having curved surfaces corresponding to the condyle parts of the femur part and a base plate for mounting the tibia part on a tibia. In such cases, it has been known to have the bearing surfaces of the femur part and tibia part shaped so as to accommodate the various types of movement which occur in a knee joint. Other types of knee joint prostheses have been known such as described in U.S. Pat. No. 4,340,978 and Swiss Patent 674,798. However, in such prostheses, practical experience has shown that, in the course of time, the intermediate parts suffer unacceptably high abrasion. In addition, particles of these parts can migrate into the living tissue surrounding the knee joint with the result of unwanted inclusions and thus disorders and damage.

It has also been known, for example, from British Patent 1,527,498, German OS 2933174 and French Patent 2,550,936 to provide bone implants with inserts of wear-resistant material between relatively movable parts.

It is an object of this invention to reduce or substantially avoid abrasion in a plastic part of a tibia part of the knee joint prosthesis.

It is another object of the invention to be able to distribute loads within a knee joint prosthesis in a manner to reduce wear in the parts of the prosthesis.

Briefly, the invention provides a knee joint prosthesis which is comprised of a femur part, a tibia part and a plurality of support members for the femur part in the tibia part.

The femur part is constructed so as to have at least one condyle with a first bearing surface including a double convex curve in an anterior/posterior direction formed from at least two circular sectors having different radii of curvature and center points.

The tibia part is constructed with a plastic part having a second bearing surface receiving the femur condyle thereon.

The support members are disposed in the plastic part of the tibia part and are of a harder material than the plastic part of the tibia part. Each support member also has a support surface lying in the bearing surface of the plastic part with the support surface including double concave curves. Each support member is of disk-like shape and the support members are distributed within the tibia part in spaced relation to each other.

The bearing surfaces of the plastic part of the tibia part are thus provided with a number of abutments which act as abrasion-reducing load-bearing surfaces for the femur part. So as to achieve a "loading surface" which is as large as possible with the abutments, the support surfaces of the abutments are constructed to complement the load-bearing surfaces of the femur part, which have a double convex curvature, i.e., are also constructed as segments of surfaces having double convex curvature. So as to achieve a stress absorption of the support surfaces of the hard support members which has the greatest area possible both with an extended and with a flexed knee, it is advantageous if the support surfaces have two different concave curves, the radii of which correspond to the radii of the convex anterior/posterior curves of the femur condyles. In addition, the edge regions of the support surfaces have a radius corresponding to the larger radius of the condyles and the central regions having a radius corresponding to the smaller radius of the condyles. In this case, support surfaces which are segments from spherical surfaces are preferred for manufacturing reasons.

So as to facilitate the "adjustment" or "adaptation" of the support members to the load-bearing surfaces of the femur part, the contact surfaces, with which the support members are supported in depressions in the intermediate part, and/or the counter surfaces thereto—i.e., the "bases"—are dished. With support members or intermediate parts dished in this way, it is also advantageous if the shell surfaces of the support members and the counter surfaces of the depressions complementary thereto are constructed as segments from spherical surfaces. It is then possible, to a certain extent, to control the movements of the support members in the intermediate part.

As is known, the intermediate parts are in some circumstances supported so that they "float" on the tibia plate. With such constructions, it is possibly advantageous if the surface of the intermediate part near the tibia plate is also covered with metal support members, the support surfaces of which are adapted to the shape of the boundary surface between the tibia plate and intermediate part.

The support members may at least belong to the same material class as the femur part, i.e. are made of ceramics in the case of ceramic load-bearing surfaces of the femur part and are made of metal in the case of metal load-bearing surfaces of the femur part. In particular, it is possible to manufacture at least the sliding or support surfaces of the support members from the same material as the load-bearing surfaces of the femur part.

These and other objects and advantages of the invention will become more apparent from the following detailed description taken in conjunction with the accompanying drawings wherein.

Figure 1:
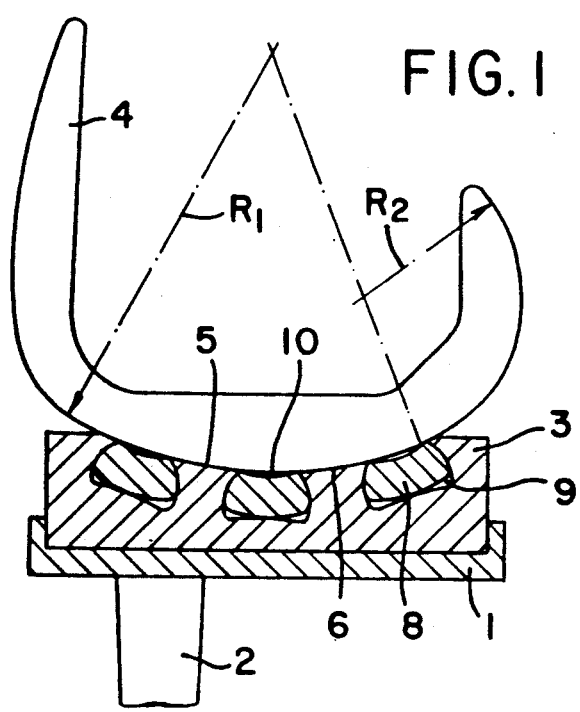
FIG. 1 illustrates a cross-sectional view of a knee joint prosthesis constructed in accordance with the invention and taken on line I—I of FIG. 2

Referring to FIG. 1, the knee joint prosthesis includes a tibia part having a metal plate 1 which can be attached by means of a peg-like shaft 2 in a tibia and an intermediate plastic part 3 which is supported on the metal plate 1. This intermediate plastic part 3 is constructed so as to act as a shock-absorbing elastic member between the normally metal tibia plate 1 and a femur part 4. This femur part 4 is only shown diagrammatically and is also usually made of metal although in some circumstances the femur part 4 may be made from a plastic, such as polyethylene, which may be fiber reinforced.

Figure 3:
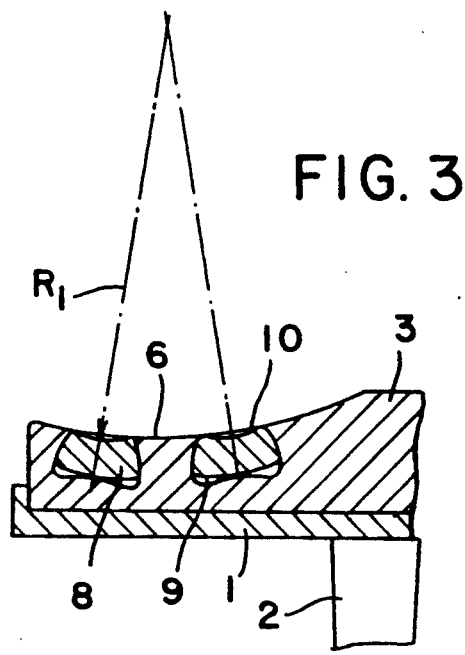
FIG. 3 illustrates a view taken on line III—III of FIG. 2.

The femur part 4 is formed with a pair of condyles each of which has a load-bearing surface 5 including a double convex curve in an anterior/posterior direction. The double convex curve is formed from two circular sectors, each having different radii of curvature R1, R2 and center points. The femur part 4, as indicated in FIG. 3, also has a concave bearing surface 6 in the medial/lateral direction for each condyle which is formed of a single curve having a radius of curvature R1 which corresponds to the larger radius of the anterior/posterior curve.

As indicated in FIG. 1, the two circular sectors of the load bearing surface 5 of the femur part 4 provide a "load bearing" surface in the standing phase of the joint as shown with the large radius R1. The circular sector having the smaller radius of curvature R2 is located at the posterior end of the bearing surface 5. This load-bearing surface comes into "use" when the knee is bent.

Figure 2:
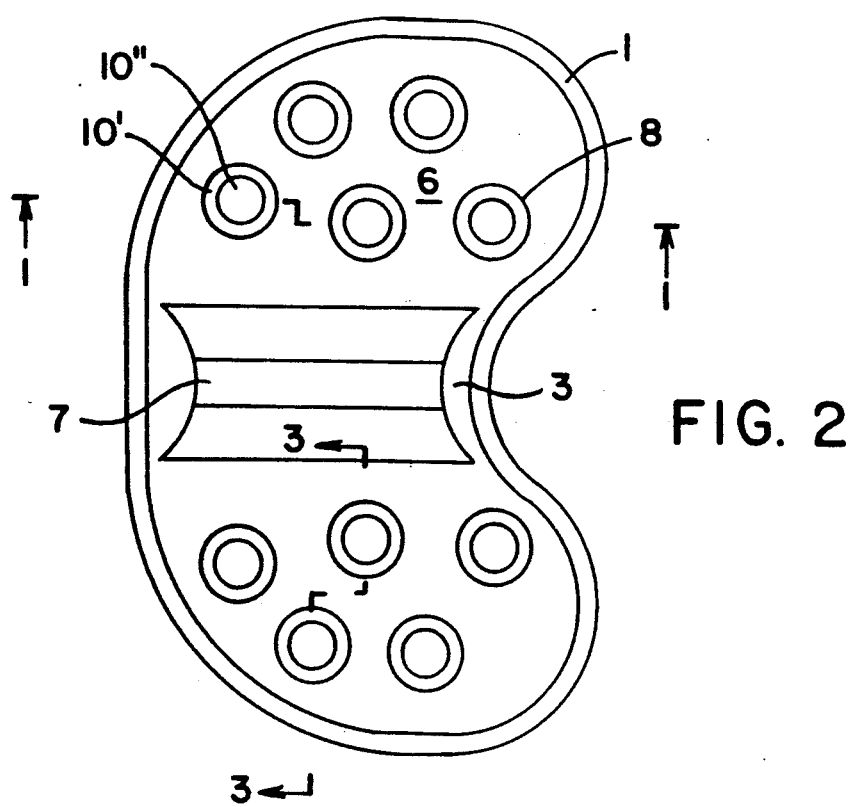
FIG. 2 illustrates a plan view of the tibia part of a knee joint prosthesis constructed in accordance with FIG. 1.

As indicated in FIG. 2, the medial/lateral bearing surface 6 represents a segment from a hollow spherical surface. For lateral guidance of the femur part 4, the intermediate plastic part 3 is provided with a bead-like protrusion 7 between the bearing surfaces 6 of the two condyles (FIG. 2).

As shown in FIGS. 1 and 2, a plurality of support members 8 are disposed in each of the bearing surfaces 6 of the intermediate plastic part 3. To this end, the intermediate plastic part 3 is provided with a plurality of depressions 9, each of which receives a support member 8 in such a way that the supporting surface 10 of the support member 8 lies in the bearing surface 6 of the plastic part 3 as accurately as possible. At least the support surfaces 10 of the support members 8 are made from a material which is relatively hard in comparison with the plastic of the intermediate part 3. Further, this material belongs at least to the same material class or is preferably the same as the material of the load-bearing surfaces 5 of the femur part 4.

The support surfaces 10, which are integrated as exactly as possible in the bearing surface 6 of the intermediate part 3, have their shape adapted to the load-bearing surfaces 5 of the femur part 4. They are therefore constructed as segments from spherical surfaces, with an edge region 10' (FIGS. 2 and 4) comprising a radius which corresponds to the radius R1 of the anterior/posterior curvature of the condyle load-bearing surfaces 5 in the standing phase, whereas a central region 10" (FIG. 2 and 4) of each support surface 10 has the radius R2 of the posterior load-bearing surface region. In this way, the support surfaces 10 fit closely to the load-bearing surfaces 5 of the femur part 4 when the knee is extended and bent, and the stresses are distributed over a relatively large total area.

Figure 4:
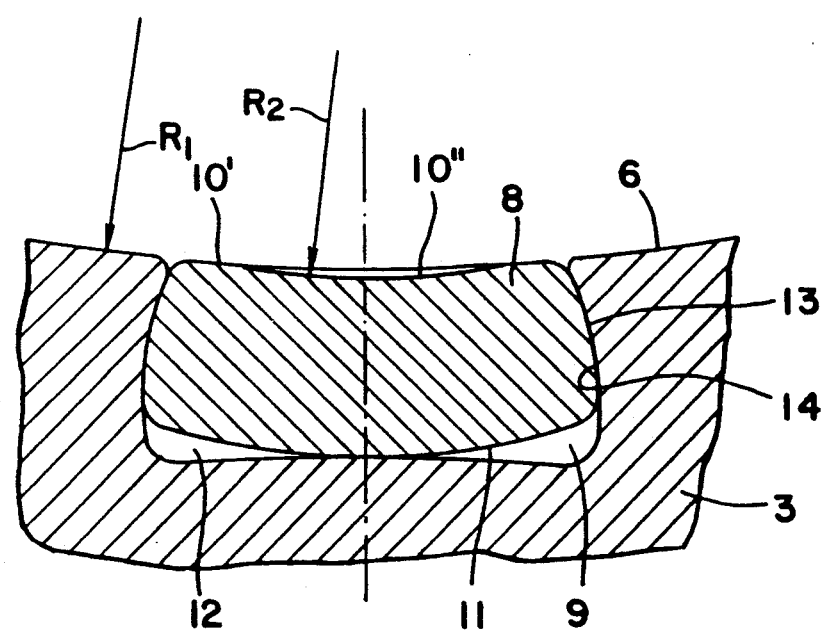
FIG. 4 illustrates a detail of FIG. 1 on an enlarged scale.

Referring to FIG. 4, each support member has a contact surface 11 which is supported on a counter surface or "base" 12 of the depressions 9 of the intermediate part 3. This counter-surface 12 is also dished. Consequently, the relative movements of the support members 8 with respect to the intermediate part 3, and consequently, the abutment of the support surfaces 10 against the load-bearing surfaces 5, are facilitated. So as to guide these relative movements, both the shell surfaces 13 (FIG. 4) of the support members 8, and also the surfaces 14 (FIG. 4) of the depressions 9 complementary thereto are constructed as spherical and hollow spherical surfaces, respectively.

As the femur part 4 and its load-bearing surfaces 5 are preferably made from metal, as has already been mentioned, in most cases of application, the support members 8 are also made of metal, for example, a cobalt base alloy or of another alloy customary for implants.

Figure 5:
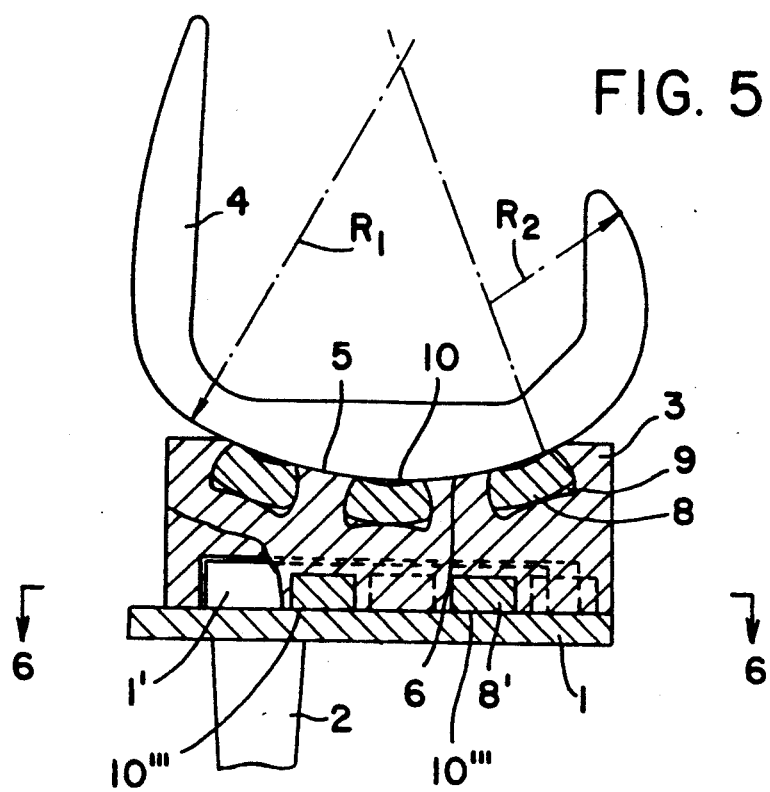
FIG. 5 illustrates a cross-sectional view of a knee join prosthesis constructed in accordance with the present invention.
Figure 6:
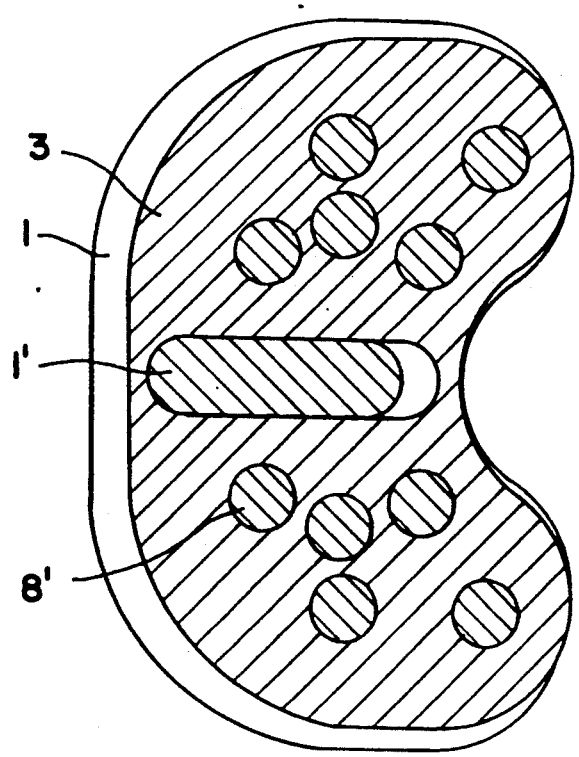
FIG. 6 illustrates a view taken on line VI—VI of FIG. 5.

In an alternative construction as shown in FIGS. 5 and 6, the tibia part may be constructed so that the intermediate plastic part 3 is supported so as to "float" on the tibia metal plate 1. In this case, the surface of the intermediate plastic part 3 facing the metal plate 1 is covered with metal support members 8' each of which has a support surface 10''' which is in facing relation to and which bears on the metal plate 1. The support surfaces 10''' are also adapted to the shape of the boundary surface between the metal plate 1 and the plastic part 3.

As indicated in FIG. 4, the two bearing surfaces of each support member 8 may be shaped so that one concave surface is complementary to the larger radius of curvature R1 of the femur part while the second concave surface is complementary to the smaller radius of curvature R2. In addition, the concave surfaces are disposed in concentric relation to each other.

The invention thus provides a knee joint prosthesis wherein wear-resistant support members can be disposed between a femur part of hard material and an intermediate plastic part of a tibia part. In addition, the invention provides support members of disc-like shape which are provided with dual load-bearing surfaces to alternately receive different load-bearing surfaces of a femur part depending upon the position of flexure of a knee joint.

What is claimed is:

1. A knee joint prosthesis comprising
a femur part having at least one condyle with a first bearing surface including a double convex curve in an anterior/posterior direction formed from at least two circular sectors having different radii of curvature and center points;
a tibia part having a plastic part with a second bearing surface receiving said at least one femur condyle thereon; and
a plurality of support members in said plastic part of a harder material than said plastic part, each said support member having a support surface lying in said bearing surface of said plastic part and including double concave curves, wherein each support surface has two different concave curves with radii of curvature correspondign to said radii of said convex anterior/posterior curves of said at least one femur condyle.

2. A knee join prosthesis as set forth in claim 1 wherein each support surface has an edge region with a radius of curvature correspondign to the larger radius of curvature of said at least one condyle and a central region with a radium of curvature correspondign to the smaller radius of curvature of said at least one condyle.

3. A knee joint prosthesis as set fort h in claim 1 wherein each support member is made of the same material as said femur part.

4. A knee join prosthesis comprising
a metal femur part having at least one condyle having a first bearing surface with a first section on a first radius of curvature and a second section in an anterior/posterior direction on a second radius of curvature;
a tibia part having a plastic part with a secondary bearing surface receiving said bearing surface of said at least on condyle thereon; and a plurality of metal support members in said plastic part, each support member having a third bearing surface lying in said second bearing surface of said plastic part with a first concave surface complementary to said first radius of curvature and a second concave surface complementary to said second radius of curvature.

5. A prosthesis as set for thin claim 4 wherein said first concave surface is concentric to and about said second concave surface.

6. A prosthesis as set forth in claim 4 which further comprises a plurality of depressions in said plastic part receiving said support members and wherein each support member has a peripheral surface of spherical shape received in mating relation in a sidewall of a respective depression.

7. A prosthesis as set forth in claim 4 wherein each support member has a convex surface received on a base surface of a respective depression.

8. A prosthesis as set forth in claim 4 wherein said first bearing surface of said at least one condyle is curved in a medial/lateral direction on a radius of curvature equal to said first radius of curvature.

9. A prosthesis as set forth in claim 4 wherein said tibia part has a metal plate receiving said plastic part in floating relation.

10. A prosthesis as set forth in claim 9 wherein said tibia part has a plurality of metal support members in said plastic part in facing relation to and bearing on said metal plate.

* * * * *

UNITED STATES PATENT AND TRADEMARK OFFICE
CERTIFICATE OF CORRECTION

PATENT NO. :  5,197,987

DATED      :  March 30, 1993

INVENTOR(S) : Koch et al.

It is certified that error appears in the above-identified patent and that said Letters Patent is hereby corrected as shown below:

```
Column 2, line 46,    change "FIG. 2" to --FIG. 2;--;
         line 55,    change "join" to --joint--;

Column 4, line 48,    change "correspondign" to --
                     corresponding--;
         line 51,    change "join" to --joint--;
         line 53,    change "correspondign" to --
                     corresponding--;
         line 55,    change "correspondign" to --
                     corresponding--;
         line 57,    change "set fort h" to --set forth--;
         line 60,    change "join" to --joint--;
         line 68,    change "on" to --one--;

Column 5, line 10,    change "for thin" to --forth in--.
```

Signed and Sealed this

Seventeenth Day of May, 1994

Attest:

BRUCE LEHMAN

Attesting Officer          Commissioner of Patents and Trademarks